US00PP28033P2

(12) United States Plant Patent
Robacker et al.

(10) Patent No.: US PP28,033 P2
(45) Date of Patent: May 16, 2017

(54) GRASS NAMED 'SEASONS IN THE SUN'

(50) Latin Name: *Schizachyrium scoparium*
Varietal Denomination: Seasons in the Sun

(71) Applicants: University of Georgia Research Foundation, Inc., Athens, GA (US); The United States of America, as Represented by the Secretary of Agriculture, Washington, DC (US)

(72) Inventors: Carol D. Robacker, Peachtree City, GA (US); Melanie L. Harrison, Griffin, GA (US)

(73) Assignees: University of Georgia Research Foundation, Inc., Athens, GA (US); The United States of America, as Represented by the Secretary of Agriculture, Washington, DC (US)

( * ) Notice: Subject to any disclaimer, the term of this patent is extended or adjusted under 35 U.S.C. 154(b) by 0 days.

(21) Appl. No.: 14/998,807

(22) Filed: Feb. 19, 2016

(51) Int. Cl.
*A01H 5/12* (2006.01)

(52) U.S. Cl.
USPC ..... Plt./384

(58) Field of Classification Search
USPC ..... Plt./384
See application file for complete search history.

*Primary Examiner* — Annette Para
(74) *Attorney, Agent, or Firm* — Klarquist Sparkman, LLP

(57) ABSTRACT

The new variety *Schizachyrium scoparium* 'Seasons in the Sun' is tough, adaptable, and drought tolerant with purple and green foliage and with an upright rounded growth habit with cascading foliage. The asexually reproduced variety is reliably propagated vegetatively.

9 Drawing Sheets

Latin name of the genus and species of the plant claimed: *Schizachyrium scoparium.*

Variety denomination: The new *Schizachyrium scoparium* claimed is of the cultivar denominated 'Seasons in the Sun'.

BACKGROUND OF THE INVENTION

The present invention relates to a new and distinct cultivar of *Schizachyrium scoparium* hereinafter referred to by the varietal domination 'Seasons in the Sun'.

The new *Schizachyrium* is a product of a planned breeding program conducted by the Inventors in Griffin, Ga. The objective of the *Schizachyrium* breeding program is to produce a tough and adaptable drought-tolerant plant with commercial value. This cultivar has significant commercial and home gardener appeal with its attractive foliage and low maintenance requirements. These and other qualities are enumerated herein.

Pedigree and history: In 2006, thirty-seven accessions (number of plants per accession ranged from one to 51 depending upon the germination of individual accessions) of *Schizachyrium scoparium* were germinated and transplanted into field plots in Griffin, Ga. After a two-year evaluation period, seeds from open pollination within accessions were collected and sown in 2008, yielding 368 seedlings. The 368 seedlings were evaluated in containers in a screenhouse in Griffin, Ga. A seedling was selected for further evaluation and labeled 'B20-10'. In 2010, this selected plant was asexually propagated by root division in Griffin, Ga., and subsequently planted into field plots in Griffin and Blairsville, Ga. in 2011. The new variety 'B20-10', now named 'Seasons in the Sun', has been tested since 2011 in Griffin and Blairsville, Ga.

SUMMARY OF THE INVENTION

The following traits have been repeatedly observed and represent the characteristics of a new variety *Schizachyrium*

*scoparium*, 'Seasons in the Sun'. The new variety 'Seasons in the Sun' has not been observed under all possible environmental conditions. The phenotype may vary somewhat with variations in, for example, temperature, day-length, light intensity, soil types, and water and fertility levels without, however, any variance in genotype.

Asexual reproduction of the new *Schizachyrium* 'Seasons in the Sun' by root division since 2010 has shown that the unique features of this new *Schizachyrium* are stable and reproduced true to type in successive generations.

'Seasons in the Sun' plants, along with the cultivars 'MinnblueA' (U.S. Plant Pat. No. 17,310) and 'Carousel' (U.S. Plant Pat. No. 20,948) have been evaluated since 2011 in field plots at Griffin, Ga. and Blairsville, Ga. Height from the soil to the tip of the flowering culm, height from the soil to the top of the foliage and width were collected each year from the Griffin plants. Foliage color was assessed monthly from May to September each year.

Throughout this specification, color names beginning with a small letter signify that the name of that color, as used in common speech, is aptly descriptive. Color names beginning with a capital letter designate values based upon The R.H.S. Colour Chart, $5^{th}$ edition published by The Royal Horticultural Society, London, England.

The following traits have been consistently observed in the original plant of this new variety and in asexually propagated progeny grown from root divisions in Blairsville, and Griffin, Ga., and, to the best knowledge of the inventors, their combination forms the unique characteristics of the new variety 'Seasons in the Sun':

1. Foliage of 'Seasons in the Sun' is purple and green from May to September.
2. 'Seasons in the Sun' exhibits an upright rounded growth habit with cascading foliage.

The new variety *Schizachyrium* 'Seasons in the Sun' can be compared to the little bluestem cultivars 'Carousel' and 'MinnblueA'. Plants of the new *Schizachyrium* differ from 'Carousel' and 'MinnblueA' in the following characteristics:

1. The new variety 'Seasons in the Sun' exhibits similar total height to 'MinnblueA' but greater total height than 'Carousel'.
2. The new variety 'Seasons in the Sun' has greater average foliage height than 'Carousel'.
3. The average canopy diameter of the new variety 'Seasons in the Sun' is narrower than the canopy diameter of 'MinnblueA'.
4. The new variety 'Seasons in the Sun' is different from 'Carousel' and 'MinnblueA' in foliage growth. The new variety 'Seasons in the Sun' has cascading foliage throughout the growing season, whereas 'Carousel' and 'MinnblueA' have mostly upright pointing foliage.
5. The new variety 'Seasons in the Sun' is different from 'Carousel' and 'MinnblueA' in foliage color. The foliage of the new variety 'Seasons in the Sun' is purple and green throughout the growing season, while the foliage of 'Carousel' and 'MinnblueA' is mostly green to green-blue.

The following observations, measurements, and values describe plants grown in Griffin, Ga. 'Seasons in the Sun' was propagated via root division and grown in one-quart containers prior to planting in field plots. All data are from plants established as single stem propagules in May 2011.

The new variety 'Seasons in the Sun' has colorful purple and green cascading foliage throughout the summer, in contrast to the green to blue-green foliage of 'Carousel' and 'MinnblueA' (Table 1). 'Seasons in the Sun' was on average similar, but slightly taller in total height than 'MinnblueA'. 'Seasons in the Sun' was on average taller than 'Carousel' in total height. 'Seasons in the Sun' displayed greater foliage height than both 'MinnblueA' and 'Carousel' at the test sites in Griffin, Ga. (Table 2). 'MinnblueA' exhibited the greatest foliage width of the 'Carousel', 'MinnblueA' and 'Seasons in the Sun' varieties (Table 2). 'Seasons in the Sun' and 'Carousel' had foliage of a similar width. The overall habit or form in early summer (before flowering) of 'Seasons in the Sun' is upright rounded, appearing to be as tall as it is wide (width to height ratio is near 1). 'MinnblueA' and 'Carousel' are more broadly rounded, with width greater than foliage height (Table 3). Plant width to total height ratio in late summer (includes flowering culms) reveals that width of 'Seasons in the Sun' is less than half of the height, while width of 'MinnblueA' and 'Carousel' is more than half of their heights. The foliage height to total height ratio was observed to be similar between 'Seasons in the Sun'; 'MinnblueA' and 'Carousel' (Table 3).

At the same age of development and under the same growing conditions, 'Seasons in the Sun' is broader in width than 'Cinnamon Girl' (patent pending) and taller in total height than 'Good Vibrations' (patent pending).

'Seasons in the Sun' and 'Cinnamon Girl' have an upright rounded growth habit with cascading foliage from May to September, but the foliage of 'Good Vibrations' is upright in early summer, changing to cascading in mid-summer.

Foliage colors vary during the growing season among these three cultivars. 'Good Vibrations' in early summer has Violet-Blue N92D, 'Seasons in the Sun' has Purple N77A or Purple 79A and 'Cinnamon Girl' has Purple N79C or Greyed-Purple 187A on the distal portion of the foliage. In mid-summer, while all three cultivars have various shades of Greyed-Purple on the distal portion of the leaves, 'Good Vibrations' also has Purple N77C. In late summer, both 'Cinnamon Girl' and 'Good Vibrations' have some Yellow-Green 144A leaves, while 'Seasons in the Sun' has some Green 138B leaves. Furthermore, 'Cinnamon Girl' has some Red-Purple 59A or Red-Purple 60C foliage, colors not seen in the other cultivars.

TABLE 1

Summary of foliage colors on upper leaf surface of 'Seasons in the Sun', 'MinnblueA', and 'Carousel' in July, August, and September 2014 on field plants in Griffin, GA. Number in parentheses indicates the percentage of leaves displaying primary color.

| Cultivar | Date | Primary Color | Secondary Color |
|---|---|---|---|
| 'Seasons in the Sun' | July | Greyed-purple N187A or N187B on upper two-thirds of the leaf (100%) | Green 138B on lower third of foliage |
| | August | Greyed-purple 186C or 187A or N187B (50%) | Green 138B on entire leaf (50%) |
| | September | Purple N77C or Greyed-Purple 187A on terminal two-thirds of leaf and 138B on basal portion (80%) | Green 138B on entire leaf (20%) |
| 'MinnblueA' | July | Green N138B on entire leaf (80%) | Purple N77A on tips of foliage (20%) |
| | August | Green 137A (100%) | |
| | September | Green 137A (90%) | Greyed-purple 183B (10%) |
| 'Carousel' | July | Green (100%) | |
| | August | Green 137B (100%) | |
| | September | Green 137A or 138A (100%) | |

TABLE 2

Total height, height to top of foliage and width of 'Seasons in the Sun' and two cultivars planted into a field plot in Griffin, GA. Data were collected on Nov. 20, 2014. Numbers in parentheses are the standard deviations.

| Cultivar | Number of reps | Total height (cm) (soil to tip of flowering stem) | Foliage height (cm) | Width (cm) |
|---|---|---|---|---|
| 'Seasons in the Sun' | 5 | 105.2 (4.5) | 45.4 (5.7) | 43.6 (6.0) |
| 'MinnblueA' | 4 | 95.0 (10.1) | 36.5 (5.9) | 61 (16.4) |
| 'Carousel' | 4 | 73.8 (17) | 24.5 (9.8) | 43.5 (9.7) |

In Table 2, total plant heights were measured from ground level to the tip of the highest flowering culm. Foliage width was measure twice on each plant, the first measurement being at the widest point and the second measurement perpendicular to the first. These measurements were made on Nov. 20, 2014, in Griffin, Ga. after four growing seasons. All measurements are in cm.

TABLE 3

Relationship of plant width to foliage height, plant width to total height and foliage height to total height of 'Seasons in the Sun' and five cultivars planted into a field plot in Griffin, GA. Measurements were made on Nov. 20, 2014 on five reps of 'Seasons in the Sun', four reps of 'MinnblueA', and 'Carousel', and one plant each of 'Blaze' (unpatented), 'The Blues' (unpatented), and 'Prairie Blues' (unpatented). Numbers in parentheses are the standard deviations.

| Cultivar | Plant width/Foliage height | Plant width/Total height | Foliage height/Total height |
|---|---|---|---|
| 'Seasons in the Sun' | 0.96 (0.05) | 0.42 (0.04) | 0.43 (0.04) |
| 'MinnblueA' | 1.65 (0.22) | 0.64 (0.12) | 0.38 (.02) |
| 'Carousel' | 1.87 (0.34) | 0.60 (0.12) | 0.33 (0.08) |

TABLE 3-continued

Relationship of plant width to foliage height, plant width to total height and foliage height to total height of 'Seasons in the Sun' and five cultivars planted into a field plot in Griffin, GA. Measurements were made on Nov. 20, 2014 on five reps of 'Seasons in the Sun', four reps of 'MinnblueA', and 'Carousel', and one plant each of 'Blaze' (unpatented), 'The Blues' (unpatented), and 'Prairie Blues' (unpatented). Numbers in parentheses are the standard deviations.

| Cultivar | Plant width/Foliage height | Plant width/Total height | Foliage height/Total height |
|---|---|---|---|
| 'Blaze' | 1.20 | 0.58 | 0.49 |
| 'The Blues' | 1.50 | 0.44 | 0.30 |
| 'Prairie Blues' | 1.53 | 0.43 | 0.28 |

In Table 3, the relationship between foliage height and plant width is presented.

In summary, 'Seasons in the Sun' has more varied foliage color than 'Carousel' and 'MinnblueA' and displays an upright rounded growth habit with cascading foliage. 'Seasons in the Sun' exhibits a foliage height closely matching the plant width. In contrast, both 'Carousel' and 'MinnblueA' are broadly rounded, displaying a plant width that is greater than the plant foliage height. 'Seasons in the Sun' is similar to 'MinnblueA' in total height and foliage height, while being slightly taller than 'Carousel'. 'Seasons in the Sun' and 'Carousel' are narrower than 'MinnblueA' in foliage width.

BRIEF DESCRIPTION OF THE FIGURES

The accompanying colored photographs illustrate the overall appearance and distinct characteristics of the new variety of *Schizachyrium scoparium* 'Seasons in the Sun'. The colors in the photographs are as close as possible with the photographic and printing technology utilized.

FIGS. 4 and 5 are photographs of a 'Seasons in the Sun' plant taken on Jun. 8, 2012 in Griffin, Ga.; with FIG. 5 being an enlarged view.

FIGS. 8 and 9 are, respectively, photographs of a 'Seasons in the Sun' plant taken on Jul. 1, 2015, in Griffin, Ga.; with FIG. 9 being an enlarged view.

FIGS. 10 and 11 are, respectively, photographs of 'Carousel' (FIG. 10) and 'MinnblueA' (FIG. 11) plants taken on Jul. 1, 2015, in Griffin, Ga.

FIGS. 14 and 15, respectively, are photographs of 'Carousel' (FIG. 14) and 'MinnblueA' (FIG. 15) plants, taken on Aug. 22, 2012, in Griffin, Ga.

FIGS. 16 and 17 are photographs of a 'Seasons in the Sun' plant taken on Sep. 10, 2014, in Griffin, Ga.; with FIG. 17 being an enlarged view.

FIGS. 18 and 19 are, respectively, photographs of 'Carousel' (FIG. 18) and 'MinnblueA' (FIG. 19) plants taken on Sep. 10, 2014, in Griffin, Ga.

BOTANICAL DESCRIPTION

Figure 1:
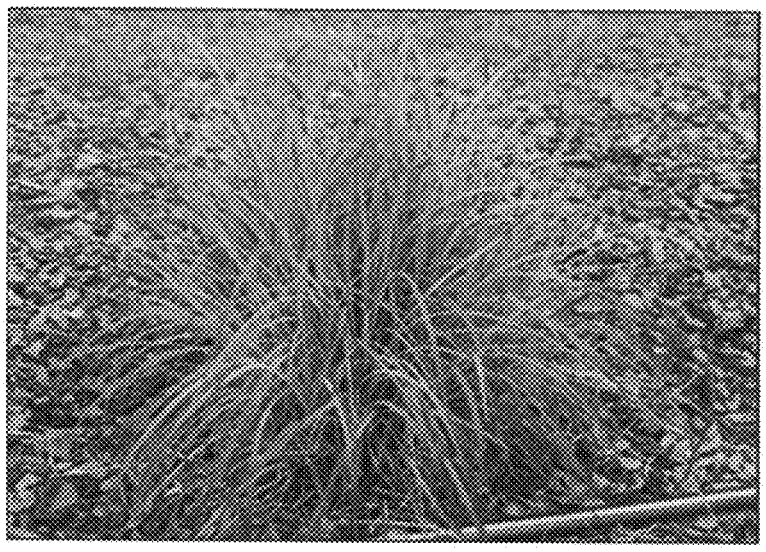
FIG. 1 is a photograph of a 'Seasons in the Sun' plant taken on May 26, 2015 in Griffin, Ga.
Figure 2:
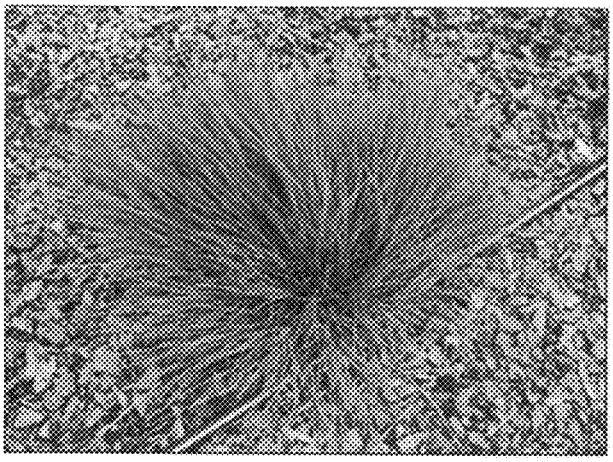
FIGS. 2 and 3 are, respectively, photographs of a 'Carousel' plant (FIG. 2) and of a 'MinnblueA' plant (FIG. 3), taken on May 26, 2015 in Griffin, Ga.
Figure 3:
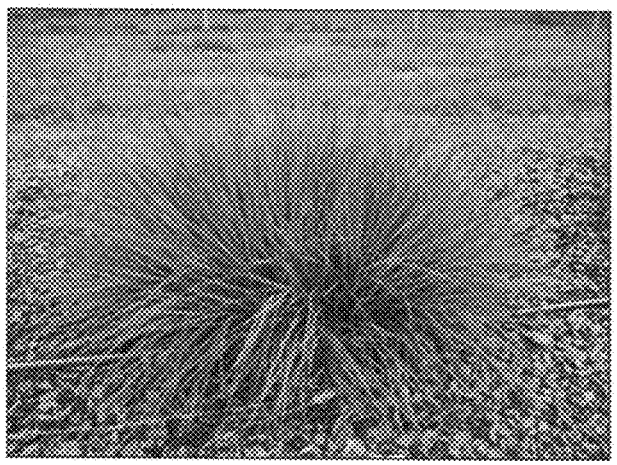
Figure 6:
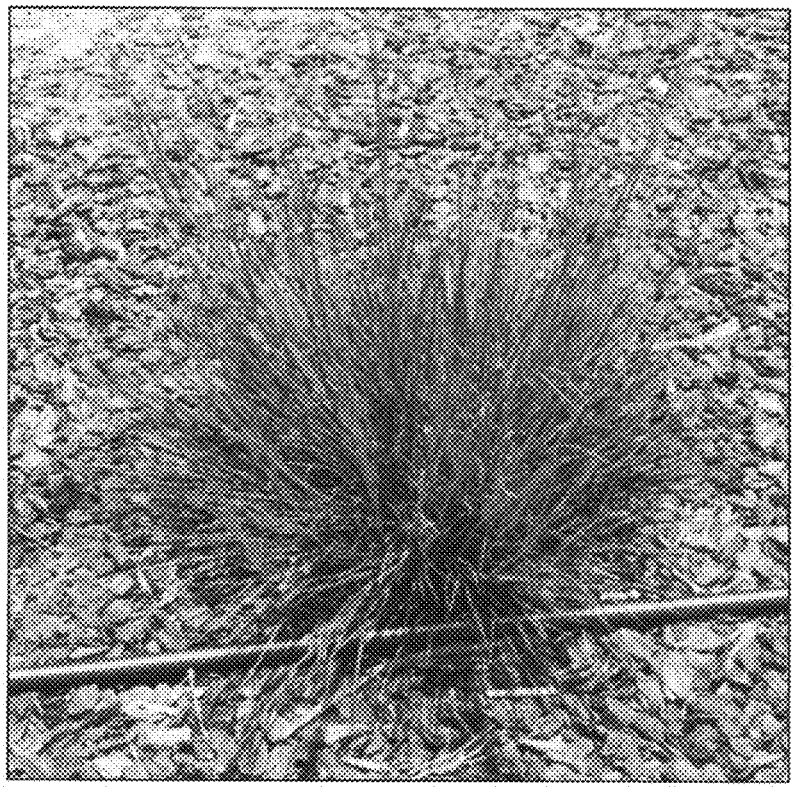
FIGS. 6 and 7 are, respectively, photographs of a 'Carousel' plant (FIG. 6) and a 'MinnblueA' plant (FIG. 7) taken on Jun. 8, 2012, in Griffin, Ga.
Figure 7:
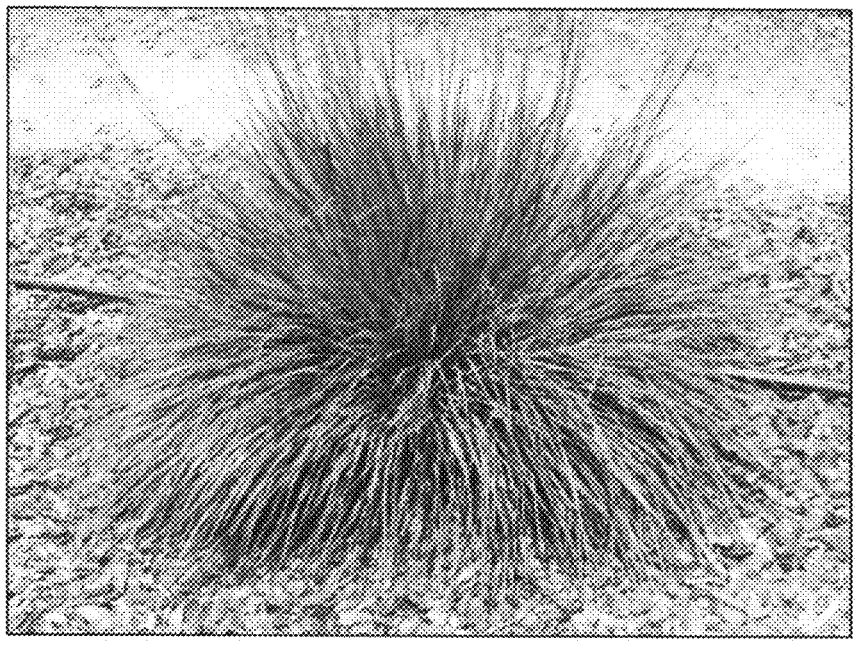
Figure 12:
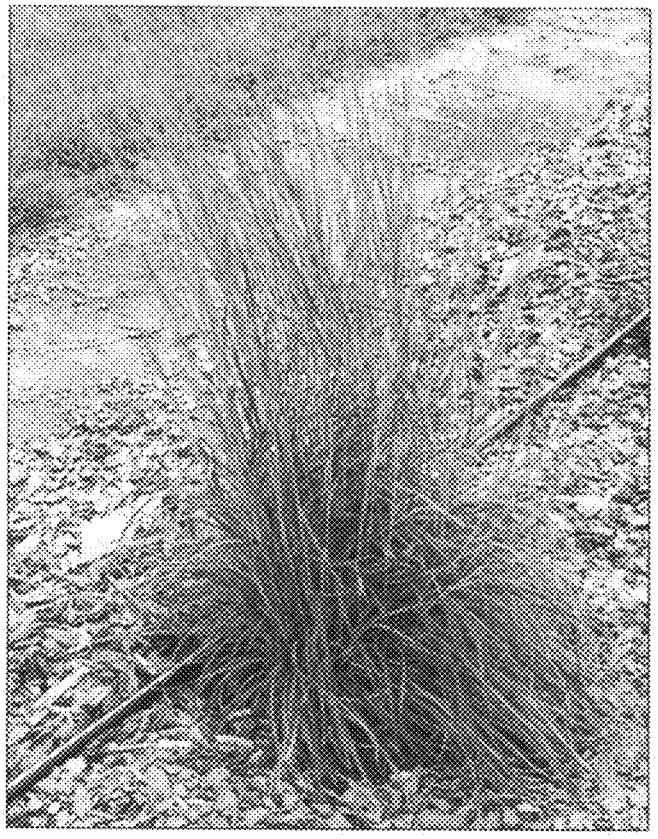
FIGS. 12 and 13 are photographs of a 'Seasons in the Sun' plant taken on Aug. 22, 2012 in Griffin, Ga.; with FIG. 13 being an enlarged view.
Figure 13:
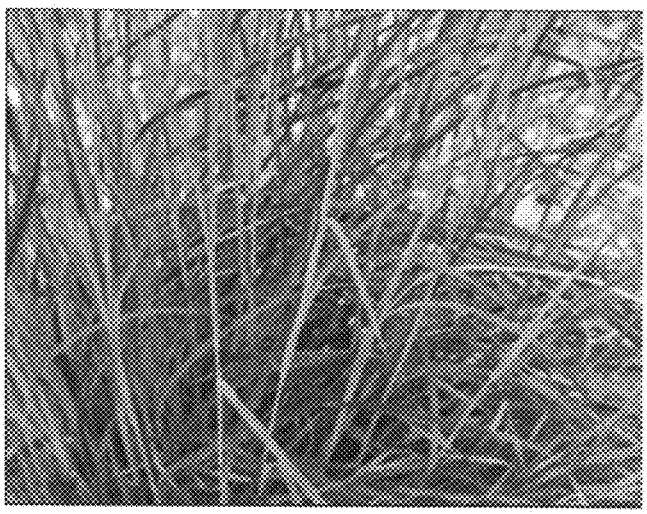

The new variety 'Seasons in the Sun' is a perennial at Griffin, Ga. (USDA Zone 8a). The new variety 'Seasons in the Sun' blooms from mid to late August. 'Seasons in the Sun' is drought tolerant and is expected to grow in USDA Zones 3-9. 'Seasons in the Sun' grows well in full sun and in most soils. The foliage is fine texture and long-lived. It appears to be genetically stable and can be propagated by root division, basal stem cutting, and tissue culture. The reproductive organs of the new variety 'Seasons in the Sun' are very small, fleeting or scarce in presence and therefore difficult to describe.

All data are from four-year-old field-grown plants established as single stem propagules in May 2011, in Griffin, Ga. Three replicated plants were grown in a randomized block design.

Plant:

*Mature plant height.*—Approximately 104 to 110 cm.

*Diameter of plant canopy.*—Approximately 35 to 53 cm.

*Foliage height.*—Approximately 41 to 52 cm.

Leaf:

*Leaf shape.*—Linear.

*Leaf division.*—Simple.

*Leaf margins.*—Entire.

*Leaf base.*—Sheathed to base of culm.

*Leaf venation.*—Parallel, color similar to foliage.

*Leaf apex.*—Acute.

*Leaf arrangement.*—Alternate, 2-ranked.

*Leaf collar type.*—Continuous.

*Leaf persistence.*—Dries but persistent through winter.

*Leaf attachment.*—Sheathed, 1 mm wide membranous ligule.

*Leaf width.*—Approximately 4 to 5 mm at base and 2 to 4 mm on blade.

*Leaf length.*—Approximately 25 to 39 cm.

*Leaf number.*—5 to 10 leaves per culm.

*Leaf surface.*—Strigillose, not waxy, with villous sheathes.

*Adaxial leaf surface trichomes.*—None.

*Abaxial leaf surface trichomes.*—None.

*Sheath trichomes.*—None.

*Adaxial leaf color.*—Early Summer: Green 143C; Purple N77A; or Purple 79A. Mid-Summer: Basal portion of the leaf is Green 138B, changing to Greyed-Purple 187A at the distal end; or basal portion is Green 138C changing to Greyed-Purple N187A or N187B at the distal portion; or basal portion is Green 139D changing to Greyed-Purple 187A at the distal portion. Late Summer: Greyed-Purple N187B; Green 138B; Greyed-Purple 187A; or Greyed-Purple N186C. Early Fall: Green 138B changing to Purple N77C at the distal end; Green 138B changing to Greyed-Purple 187A; or Green 138B.

*Abaxial leaf color.*—Early Summer: Green 138C; Greyed-Purple 189B; or Greyed-Purple N187B. Mid-Summer: Greyed-Green 191B; or Green 138B. Late Summer: Greyed-Purple N187C; or Greyed-Green 191B; or Greyed-Green 188A. Early Fall:

Green 138B changing to Greyed-Green 197B; or Violet 84C; or Green 138B.

Flower:

*Blooming period*.—Mid to late August in Griffin, Ga. with multiple racemes present per flower culm.

*Inflorescence*.—Yes.

*Inflorescence type*.—Racemes at terminus and nodes.

*Inflorescence size*.—8 to 18 cm in length, 0.5 cm in diameter.

*Inflorescence color*.—Red-Purple 59B.

*Spikelet number*.—5 to 7 per raceme.

*Spikelet size*.—3 to 7 cm long and with an internode distance of 1 to 2 cm.

*Spikelet arrangement*.—Alternately on the rachis.

*Spikelet hairs*.—Approximately 1 mm long, White N155D with a fluffy texture.

*Glumes*.—Average of 5 mm long by 1 mm wide.

*Palea*.—2 mm long and less than 1 mm wide.

*Peduncle*.—1 to 7 cm long and 0.5 to 0.7 mm diameter.

*Peduncle color*.—Greyed-Orange 165A.

Culm:

*General*.—Flat, solid.

*Stem surface*.—Glabrous towards the base, becoming strigillose as blades form.

*Pith*.—1 mm wide, Yellow-Green 153C.

*Culm color*.—Red-Purple 70C toward the base, changing to Yellow-Green 144B at the distal portion.

*Culm size*.—3 to 4 mm diameter and 7 to 13 cm in length before the blade emerges; at blooming, up to 110 cm from the base to the tip of the flower panicle.

*Internode length*.—8 cm.

What is claimed is:

1. A new and distinct variety of the *Schizachyrium* plant named 'Seasons in the Sun' as herein illustrated and described.

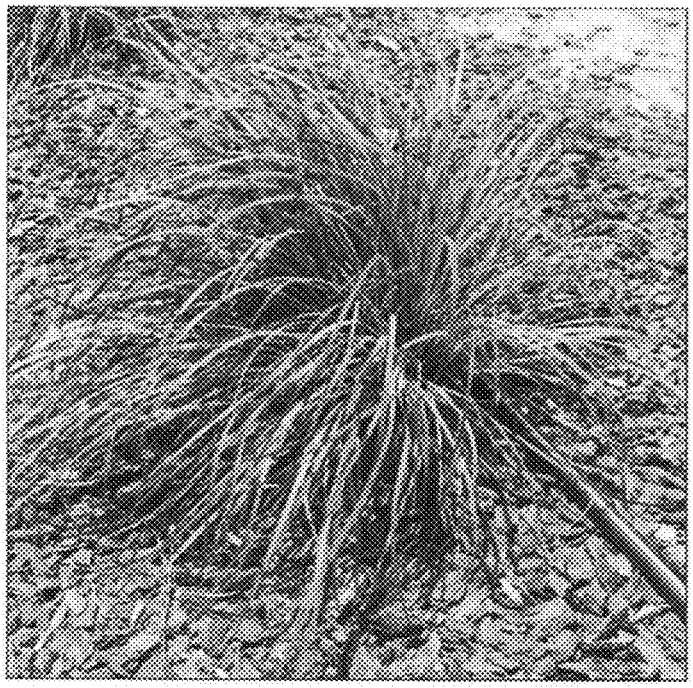
FIG. 4
FIG. 5
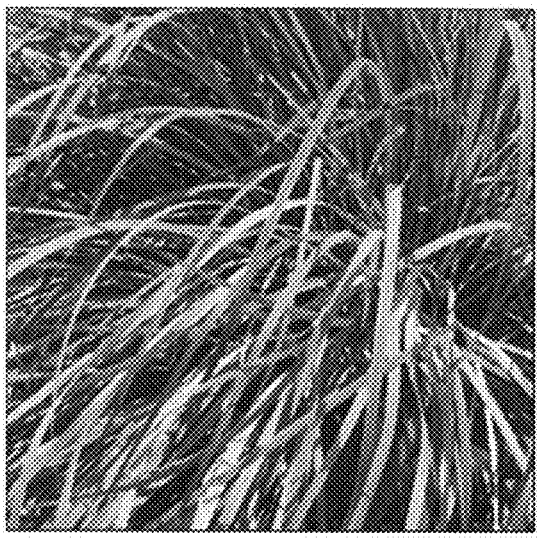

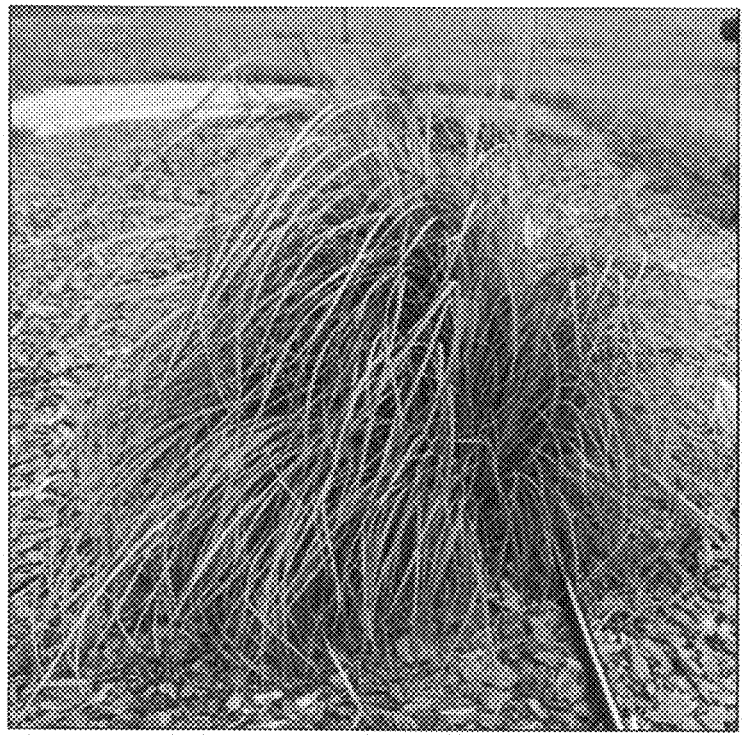
FIG. 8
FIG. 9
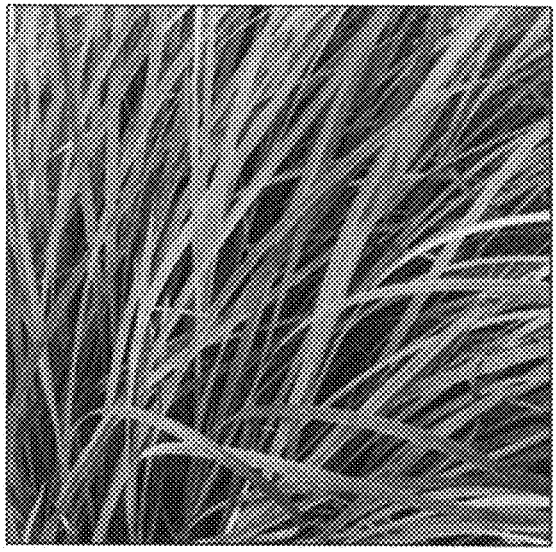

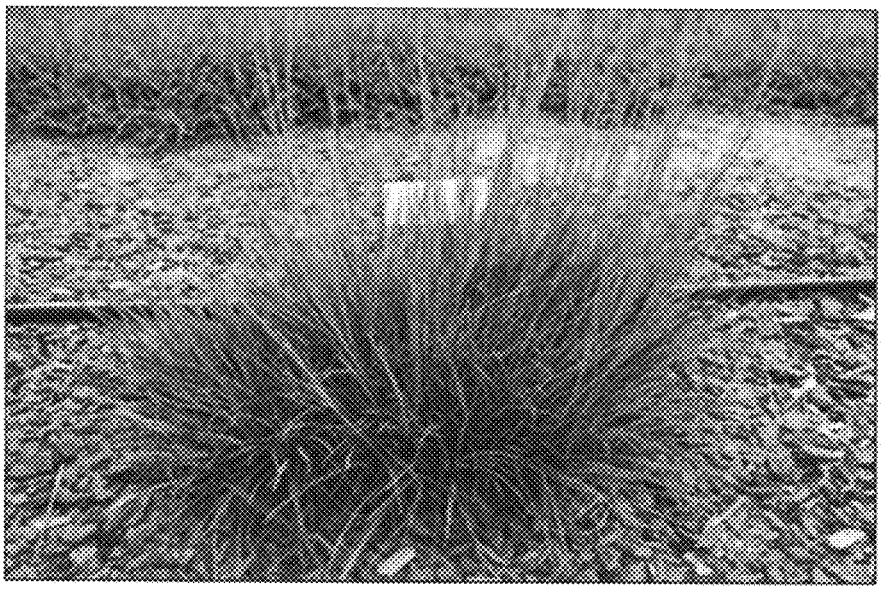
FIG. 10
FIG. 11
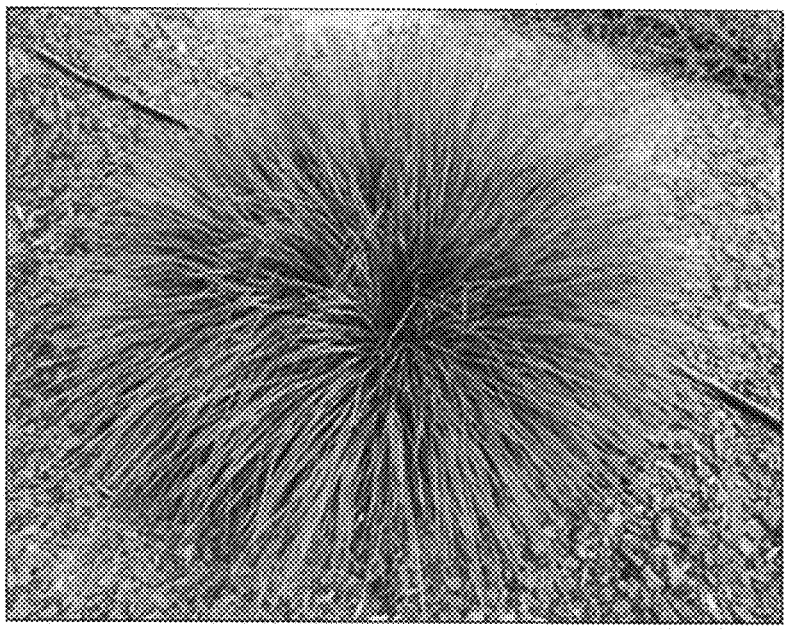

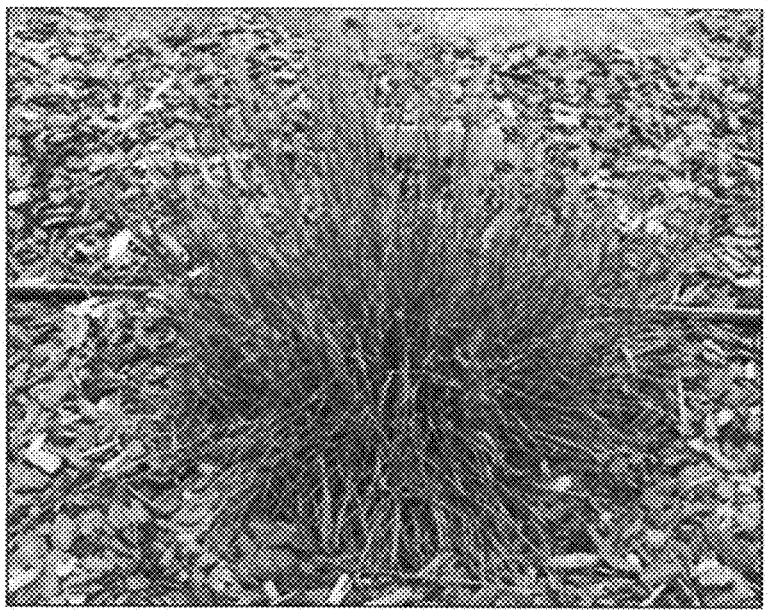
FIG. 14
FIG. 15
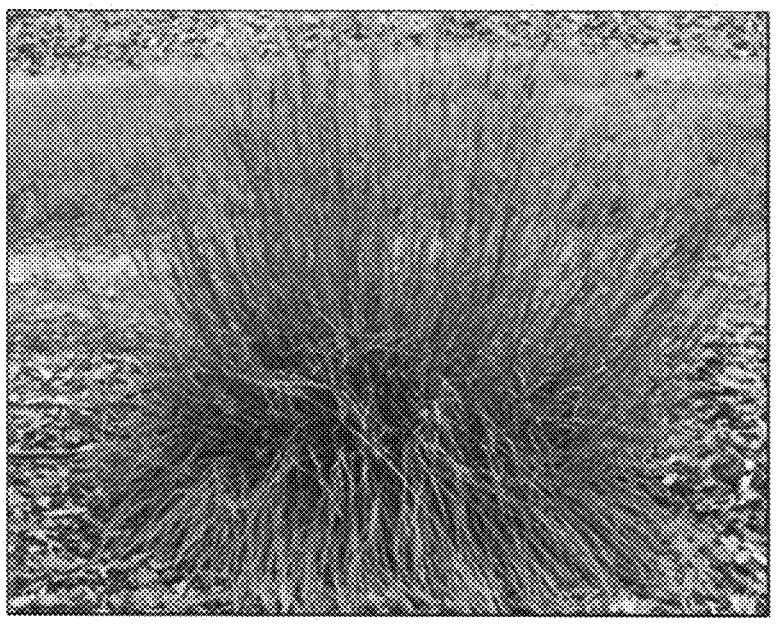

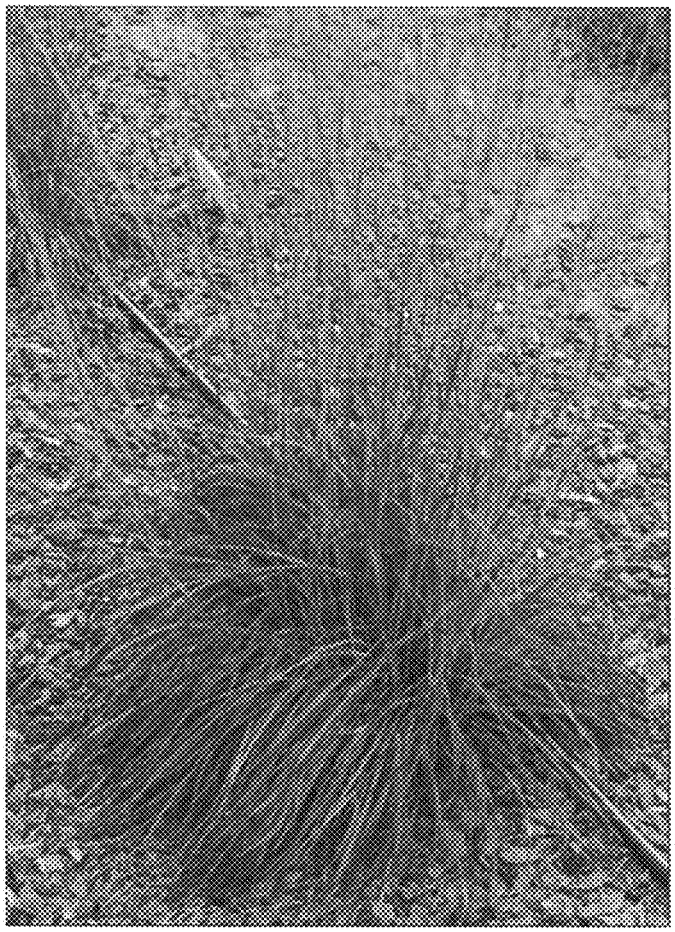
FIG. 16
FIG. 17
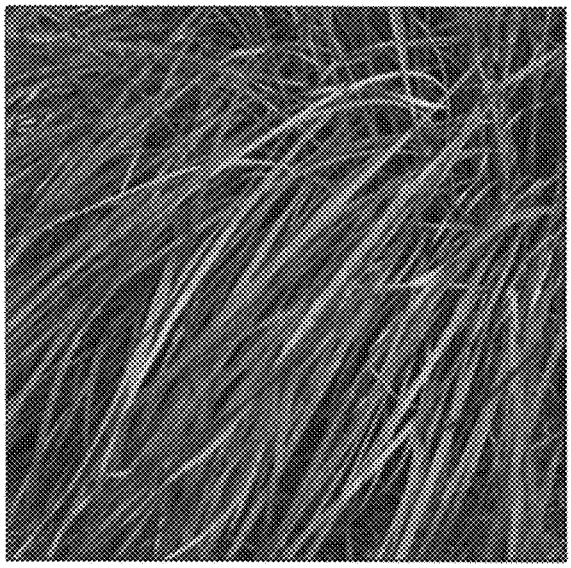

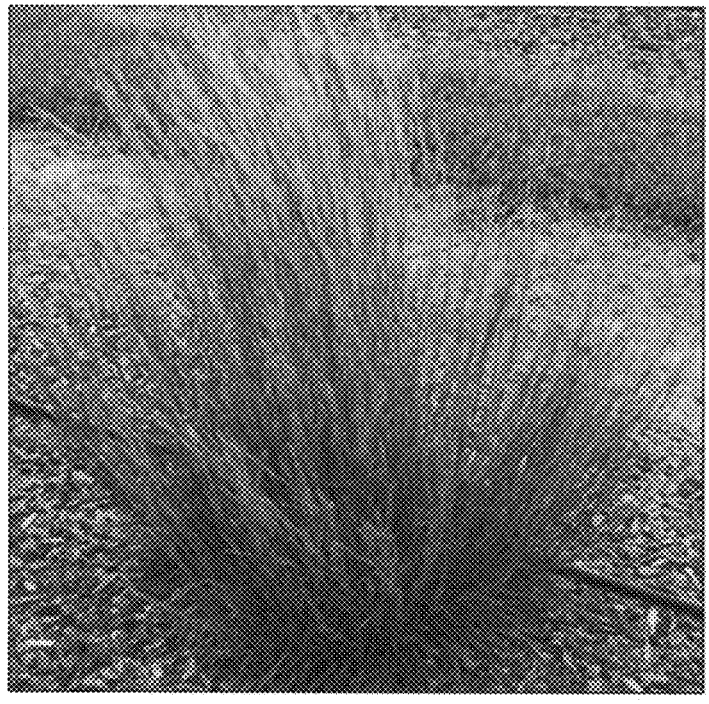
FIG. 18
FIG. 19
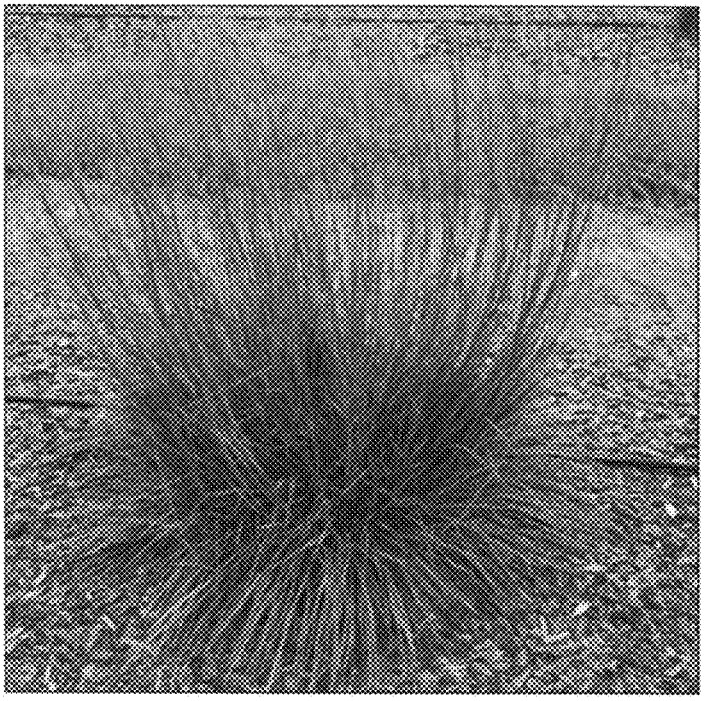

* * * * *